United States Patent
Chung et al.

(10) Patent No.: US 6,599,587 B2
(45) Date of Patent: Jul. 29, 2003

(54) ORGANOMETALLIC PRECURSOR FOR FORMING METAL PATTERN AND METHOD OF FORMING METAL PATTERN USING THE SAME

(75) Inventors: Min Chul Chung, Daejun-Shi (KR); Soon Taik Hwang, Kyungki-Do (KR); Young Hun Byun, Daejun-Shi (KR); Euk Che Hwang, Kyoungki-Do (KR)

(73) Assignee: Samsung Eleectronics Co., Ltd., Kyungki-Do (KR)

( * ) Notice: Subject to any disclaimer, the term of this patent is extended or adjusted under 35 U.S.C. 154(b) by 0 days.

(21) Appl. No.: 10/238,595

(22) Filed: Sep. 11, 2002

(65) Prior Publication Data
US 2003/0087185 A1 May 8, 2003

(30) Foreign Application Priority Data
Sep. 11, 2001 (KR) .......................... 2001-55755

(51) Int. Cl.$^7$ .................................................. B05D 3/06
(52) U.S. Cl. ................ 427/558; 427/259; 427/261; 427/282; 427/343; 427/377; 427/383.1; 427/419.2; 427/421; 427/428; 427/595; 556/112; 556/113; 556/142; 556/146
(58) Field of Search ................ 427/558, 259, 427/261, 282, 343, 377, 383.1, 419.2, 421, 428, 595; 556/112, 113, 142, 146

(56) References Cited

U.S. PATENT DOCUMENTS

| 5,064,685 A | 11/1991 | Kestenbaum et al. |
|---|---|---|
| 5,534,312 A | 7/1996 | Hill et al. |

FOREIGN PATENT DOCUMENTS

| JP | 62-263973 A | 11/1987 |
|---|---|---|

Primary Examiner—Bernard Pianalto

(74) Attorney, Agent, or Firm—Birch, Stewart, Kolasch & Birch, LLP

(57) ABSTRACT

Disclosed is an organometallic precursor for forming a metal pattern, having a structure defined by the following Formula 1, and a method of forming the metal pattern using the same, in which the conductive metal pattern is readily formed through an exposing step without using a photo-resist.

$$L'—M—L \qquad \text{Formula 1}$$

wherein, M is a transition metal selected from the group consisting of Ag, Au, Cu, Pd, Ni, and Pt; L is an imidazolylidene compound having a structure defined by the following Formula 2; and L' is an imidazolylidene compound having a structure defined by the following Formula 2 or a β-diketonate compound having a structure defined by the following Formula 3:

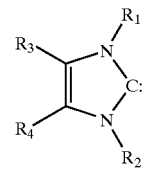

Formula 2 wherein, $R_1$, $R_2$, $R_3$, and $R_4$ are independently a hydrogen atom, or alkyl group, alkenyl group, alkynyl group, carboxyl group, alkoxy group, or ester group with 1 to 20 carbons, or aromatic hydrocarbon group with 6 to 20 carbons; and

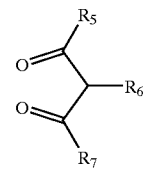

Formula 3 wherein, $R_5$, $R_6$, and $R_7$ are independently a hydrogen atom, or alkyl group, alkenyl group, alkynyl group, carboxyl group, alkoxy group, or ester group with 1 to 20 carbons, or aromatic hydrocarbon group with 6 to 20 carbons.

8 Claims, 1 Drawing Sheet

ORGANOMETALLIC PRECURSOR FOR FORMING METAL PATTERN AND METHOD OF FORMING METAL PATTERN USING THE SAME

BACKGROUND OF THE INVENTION

1. Field of the invention

The present invention relates to an organometallic precursor for forming a micro- or a nano-sized conductive metal pattern using light and without using a photo-resist and a method of forming such a metal pattern using the same. More particularly, the present invention relates to an organometallic precursor, in which at least one of two ligands combined with a central transition metal is an imidazolylidene compound and the other is a homo or hetero imidazolylidene compound or β-diketonate compound, and a method of forming the metal pattern using the same.

2. Description of the Prior Art

As well known to those skilled in the art, a conventional method of forming a metal pattern comprises the steps of depositing metal organics on a silicone or glass substrate according to a chemical vapor deposition process or an atomic layer deposition process to form a film on the substrate; coating a photo-resist on the resulting substrate according to a spin coating process; patterning the coated substrate according to a photolithography process; and etching the patterned substrate to remove the photo-resist. Another conventional method of forming a metal pattern comprises the steps of forming a metal film on a substrate according to a plasma deposition process, a sputtering process, or an electric plating process; coating a photosensitive resin on the resulting substrate; patterning the coated substrate using light; and etching the patterned substrate to form a desired metal pattern. These conventional methods require a high temperature and vacuum devices, and a patterning step using the photo-resist and an etching step for removing the photo-resist.

Meanwhile, various methods of forming a metal pattern without using a photoreaction have been suggested. For example, Japanese Patent Publication No. 62-263973 discloses a method of forming a metal pattern, in which an electronic beam is irradiated to an organometallic compound thin film without inducing any photoreaction. In addition, U.S. Pat. No. 5,064,685 (Kestnbaum et al.) discloses a method of forming a metal film using a thermal decomposition reaction, comprising the steps of coating metal organic ink on a substrate; and heating the resulting substrate with the use of a laser beam. According to this patent, the substrate is exposed to a high temperature, and materials other than metals are not allowed to be deposited on the substrate.

Another example of a method of forming a metal pattern is proposed by U.S. Pat. No. 5,534,312 (Hill, et al.), in which organic compounds sensitive to light are coordinate-bonded to a metal to synthesize an organometallic compound, the organometallic compound thus synthesized is coated on a substrate, and the resulting substrate is irradiated by the light to form a metal pattern without performing a coating step using a photo-resist. An organic ligand compound used in the above method is selected from the group consisting of acetylacetonates, dialkyldithiocarbamates, carboxylates, pyridines, amines, diamines, arsines, diarsines, phosphines, diphosphines, arenes, and alkoxy ligands. One or more ligands selected from the group consisting of oxalato, halogen, hydrogen, hydroxy, cyano, carbonyl, nitro, nitrate, nitrosyl, ethylene, acetylene, thiocyanato, isothiocyanato, aquo, azide, carbonato, amine, and thiocarbonyl are combined with a metal alone or in combination with two or more of the above organic ligand compounds to synthesize the organometallic compound. According to this patent, when the organometallic compound thus synthesized is coated on the substrate and exposed through a patterned mask, the light is directly reacted with the organometallic compound to decompose organic ligands coordinate-bonded to the metal to separate the organic ligands from the metal and to react the metal with surrounding metal atoms or oxygen in the atmosphere to form a metal oxide film pattern. Furthermore, the oxide film thus formed is subjected to a reduction reaction and a surface heat treatment under a mixed gas of hydrogen with nitrogen at 200° C. or higher so as to improve the conductivity of the oxide film. However, the method disclosed in the above patent is disadvantageous in that the organometallic compound consists of ligands having a relatively high steric hindrance. This means that a space vacated by the ligand decomposed by the light is large, thereby undesirably increasing a shrinkage of a metal film thickness. So, the shrinkage of the metal film produced according to the above method reaches 90%, thus causing problems such as cracking and crazing of the metal film.

SUMMARY OF THE INVENTION

Therefore, it is an object of the present invention to avoid the above disadvantages, and to provide an organometallic compound in which the bulkiness of organic ligands, the primary cause of a metal film shrinkage, is reduced and the ligands are readily decomposed by light to separate from metals, and a method of forming a metal pattern using the organometallic compound.

According to an aspect of the present invention, provided is an organometallic precursor for forming a metal pattern, having a structure defined by the following Formula 1:

Formula 1 wherein, M is a transition metal selected from the group consisting of Ag, Au, Cu, Pd, Ni, and Pt; L is an imidazolylidene compound having a structure defined by the following Formula 2; and L' is an imidazolylidene compound having a structure defined according to Formula 2 or a β-diketonate compound having a structure defined by the following Formula 3:

Formula 2

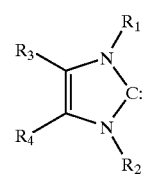

wherein, $R_1$, $R_2$, $R_3$, and $R_4$ are independently a hydrogen atom, or alkyl group, alkenyl group, alkynyl group, carboxyl group, alkoxy group, or ester group with 1 to 20 carbons, or aromatic hydrocarbon group with 6 to 20 carbons; and

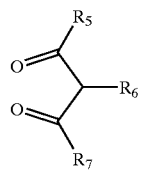

Formula 3 wherein, $R_5$, $R_6$, and $R_7$ are independently a hydrogen atom, or alkyl group, alkenyl group, alkynyl group, carboxyl group, alkoxy group, or ester group with 1 to 20 carbons, or aromatic hydrocarbon group with 6 to 20 carbons.

According to another aspect of the present invention, a method of forming a metal pattern using such an organometallic precursor is provided.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

The priority Korean Patent Application No. 2001-55755 filed on Sep. 11, 2001 is hereby incorporated in its entirety by reference.

An organometallic precursor of the present invention is a compound in which two ligands are combined with a central metal, at least one of two ligands is an imidazolylidene compound, and the other is a homo or hetero imidazolylidene compound or β-diketonate compound. The organometallic precursor of the present invention is defined by Formula 1, below:

L'—M—L     Formula 1 wherein, M is a transition metal selected from the group consisting of Ag, Au, Cu, Pd, Ni, and Pt; L is an imidazolylidene compound having a structure defined by the following Formula 2; and L' is an imidazolylidene compound having a structure defined according to Formula 2 or a β-diketonate compound having a structure defined by the following Formula 3:

Formula 2

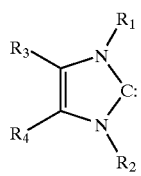

wherein, $R_1$, $R_2$, $R_3$, and $R_4$ are independently a hydrogen atom, or alkyl group, alkenyl group, alkynyl group, carboxyl group, alkoxy group, or ester group with 1 to 20 carbons, or aromatic hydrocarbon group with 6 to 20 carbons; and

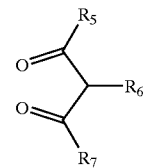

Formula 3 wherein, $R_5$, $R_6$, and $R_7$ are independently a hydrogen atom, or alkyl group, alkenyl group, alkynyl group, carboxyl group, alkoxy group, or ester group with 1 to 20 carbons, or aromatic hydrocarbon group with 6 to 20 carbons.

Figure 1:
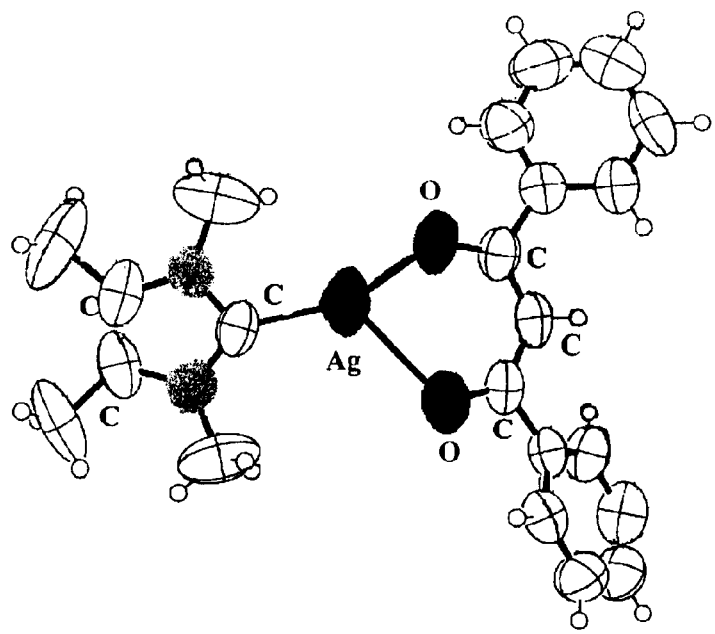
FIG. 1 schematically illustrates a molecular structure of (1,3-dimethyl-4,5-dimethylimidazole-2-ylidene)(diphenylacetonate)silver produced according to the present invention.

The organometallic precursor of the present invention has a peculiar molecular structure. For example, the molecular structure of (1,3-dimethyl-4,5-dimethylimidazol-2-ylidene)(diphenylacetonate)silver which will be described in preparation example 4 is illustrated in FIG. 1. With reference to FIG. 1, the imidazolylidene and diketonate ligand and the central metal are all positioned on the same plane, and only phenyl groups connected to the diketonate ligand are slightly deviated from the plane.

Figure 2:
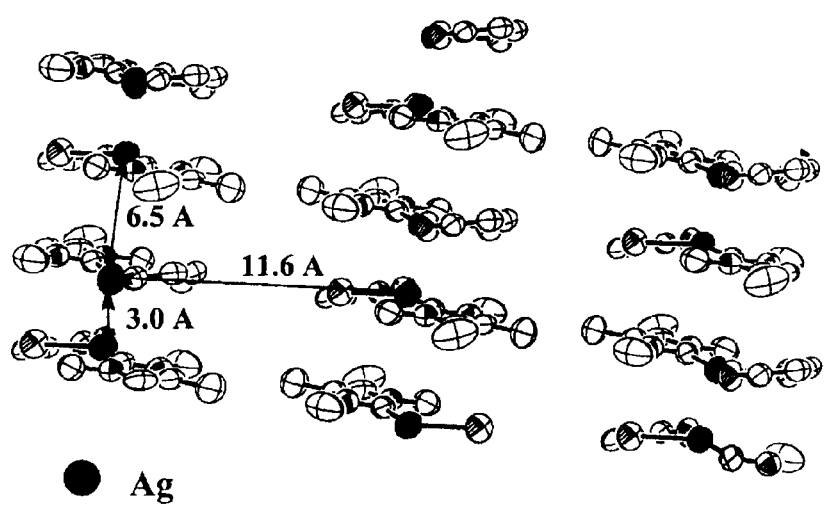
FIG. 2 schematically illustrates a molecular arrangement of (1,3-dimethyl-4,5-dimethylimidazole-2-ylidene)(diphenylacetonate)silver produced according to the present invention.

In addition, a molecular arrangement of (1,3-dimethyl-4,5-dimethylimidazol-2-ylidene)(diphenylacetonate)silver having the molecular structure of FIG. 1 is shown in FIG. 2. The phenyl group and a hydrogen atom of a diphenylacetonate ligand are omitted in FIG. 2. As shown in FIG. 2, each molecule is layered in such a way that each ligand is at 180 angles with other ligands due to steric hindrance between ligands. In addition, central metals are vertically layered in a repeating pattern in such a way that a first central metal is positioned at a distance of 3 Å from a second central metal, similar to a van der Waals bonding length (van der Waals bonding length: 2.82 Å), and the third central metal is positioned at a distance of 6.5 Å from the second central metal. Then, a fourth central metal is positioned 3 Å from the third central metal, and so on in a repeating fashion. Furthermore, central metals are horizontally positioned in a zigzag arrangement.

As described above, the present invention is advantageous in that a shrinkage of a metal film is low during patterning because two organic ligands are positioned on the same plane as each central metal in the organometallic precursor of the invention and distances between metals are short, thereby preventing cracking and crazing of the metal.

Another advantage of the present invention is that a separate photo-resist coating step and an etching step are not needed because the organic ligands constituting the organometallic precursor of the present invention are sensitive to light and so they are easily separated from the central metals and easily decomposed during an exposing step.

According to another aspect of the present invention, provided is a method of forming a metal pattern using the organometallic precursor, comprising the steps of dissolving the organometallic precursor in a solvent; coating the resulting solution on a substrate to form a thin film; exposing the thin film through a mask; and developing the thin film to form a metal or metal oxide pattern on the substrate. When the organometallic precursor of the present invention is exposed to light, organic ligands (L and L') connected to metals (M) are separated from the metals and decomposed, and the metals remaining on the substrate are combined with each other to form the metal pattern. Therefore, an organometallic thin film exposed to light is converted into a metal thin film, and a portion of the organometallic thin film not exposed to the light and photo-decomposed organics are dissolved in an organic solvent during the developing step, thus being easily removed.

Illustrative, but non-limiting examples of the substrate useful to form the metal pattern according to the present invention include an inorganic material substrate such as a silicone or glass substrate, an organic material substrate such as a plastic substrate, or a substrate made of a composite of the inorganic material with the organic material.

In addition, the coating step is preferably conducted according to a spin coating process, a roll coating process, a micro-contact printing process, or a spray coating process, and the exposing step is conducted using ultraviolet light as a source of light.

Further, the above method may further comprise the step of annealing the metal or metal oxide pattern after the developing step. According to the present invention, the annealing step may be conducted at a relatively low temperature at which the substrate consisting of glass or plastics is thermally less affected, and if necessary, under a mixed gas atmosphere of hydrogen with nitrogen, a pure nitrogen gas atmosphere, or an air atmosphere at 300° C. or lower, preferably 200° C. or lower.

The method can be applied to replace a sputter layer of a flexible display or a flat panel display, or to a CMP-free damascene process and a PR-free ITO layer forming process.

A better understanding of the present invention may be obtained in light of the following examples which are set forth to illustrate, but are not to be construed to limit the present invention.

Preparation Example 1

Synthesis of 1,3-dimethyl-4,5-dimethylimidazole-2-thione

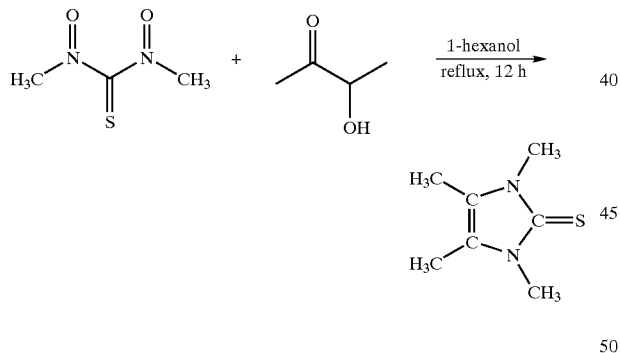

1,3-dimethyl-4,5-dimethylimidazole-2-thione was synthesized according to a method obtained by modifying a method suggested by N. Kuhn, et al. (N. Kuhn and T. Kratz, Synthesis, June 1993, p.561), and a procedure of synthesizing the same is described below. 100 mmol of dimethylthiourea and 100 mmol of 3-hydroxyl-2-butanone were added to 250 ml of 1-hexanol in order, and then subjected to a reflux reaction for about 12 hours while increasing a reaction temperature to 150 to 160° C. At this time, white solid reactants were dissolved in 1-hexanol to be partly converted into yellow solid reactants according to an increase in the reaction temperature. After a completion of the reflux reaction, the resulting solution was left in a freezer at about −30° C. for about one day to separate into a white solid component and a yellow liquid component. The yellow liquid component was removed by use of a syringe, and the remaining white solid component was rinsed with water and ether and dried to produce 1,3-dimethyl-4,5-dimethylimidazole-2-thione. 1,3-dimethyl-4,5-dimethylimidazole-2-thione thus produced was analyzed by a $^1$H-NMR analyzer and the results are as follows:

$^1$H-NMR(CD$_2$Cl$_2$): 3.48 [s, 6H, N(1,3)—CH$_3$], 2.06 [s, 6H, C(4,5)—CH$_3$]

Preparation Example 2

Synthesis of 1,3-dimethyl-4,5-dimethylimidazole-2-ylidene

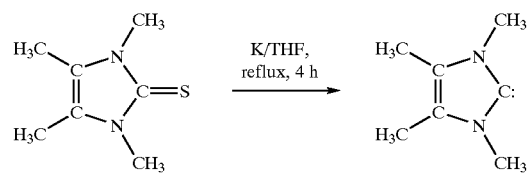

5 mmol of 1,3-dimethyl-4,5-dimethylimidazole-2-thione obtained from preparation example 1 was dissolved in 30 ml of THF and cooled to 0° C. 2.2 equivalents of finely cut potassium metal was then added to the resulting THF. The resulting solution was heated and subjected to a reflux reaction for about 4 hours. After a completion of the reflux reaction, a light yellow liquid component was separated from the solution with the use of a filter paper tied to an end of a needle. A solvent was then removed to yield light yellow 1,3-dimethyl-4,5-dimethylimidazol-2-ylidene, and 1,3-dimethyl-4,5-dimethylimidazol-2-ylidene thus produced was stored under a nitrogen atmosphere at a low temperature and analyzed by a $^1$H-NMR analyzer. The results are as follows:

$^1$H-NMR(C$_6$D$_6$): 3.35 [s, 6H, N(1,3)—CH$_3$], 1.59 [s, 6H, C(4,5)—CH$_3$]

Preparation Example 3

Synthesis of diphenylacetonate silver

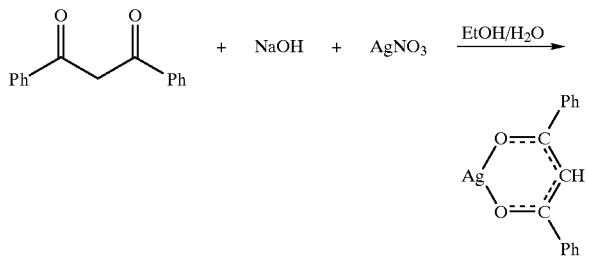

4.54 g of 1,3-diphenyl-1,3-propandione (or dibenzoyl methane) and 0.8 g of NaOH were added to a 20 ml of ethanol/60 ml of water solution in order, and the resulting mixture was reacted at a room temperature for about 2 hours to produce a yellow liquid. The yellow liquid thus produced was slowly added in drops to 80 ml of aqueous solution containing 3.44 g of AgNO$_3$ to form a grey solid component. After the resulting solution was agitated for one hour, the grey solid was filtered, rinsed with water, ethanol, and ether in order, and dried in a vacuum oven at 50° C. for about 6 hours to produce diphenylacetonate silver. Diphenylacetonate silver thus produced was analyzed by an IR spectrometry to confirm an existence of a C═O bond, and the results are as follows:

FT-IR(KBr): 1420, 1455, 1509, 1560, 1597 cm$^{-1}$

Preparation Example 4

Synthesis of [(1,3-dimethyl-4,5-dimethylimidazol-2-ylidene)(diphenylacetonate)silver]

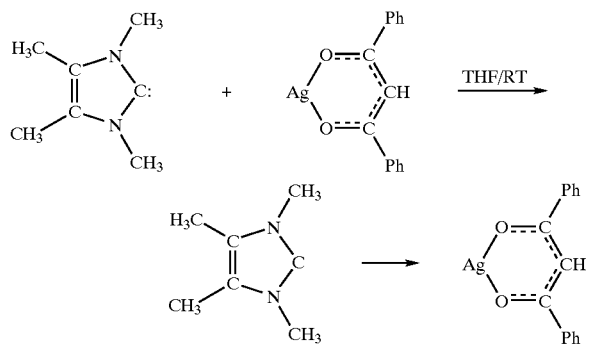

281 mg of 1,3-dimethyl-4,5-dimethylimidazol-2-ylidene (2.267 mmol) obtained from preparation example 2 was added to 30 ml of THF solvent with agitation under a nitrogen atmosphere to be dissolved in the THF solvent. The resulting THF solution of 30 ml was cooled to a low temperature of −78° C., and 749 mg of diphenylacetonate silver slurry obtained from preparation example 3 was slowly added to the cooled THF solution and slowly heated to a room temperature over about 3 hours while agitating the cooled THF solution. Fine black precipitates in the solution were then removed by use of a celite, and a solvent was removed under a vacuum to produce a solid. The solid thus produced was dissolved in about 20 ml of methylene chloride and left in a freezer at −30° C. for about one day, and a half of supernatant liquid was slowly added to 100 ml of pentane or hexane solvent by use of a syringe to form a grey solid. After the pentane or hexane solvent containing the grey solid was left for about 1 hour to sufficiently precipitate the grey solid component, a light yellow supernatant liquid was removed by use of the syringe. About 50 to 60 ml of hexane and the remaining methylene chloride solution were added to form the grey solid. As described above, after a solution containing the grey solid was left for about 1 hour to sufficiently precipitate the grey solid, a light yellow supernatant liquid was removed by use of the syringe to produce (1,3-dimethyl-4,5-dimethylimidazole-2-ylidene)(diphenylacetonate)silver. A yield of (1,3-dimethyl-4,5-dimethylimidazole-2-ylidene)(diphenylacetonate) silver thus produced was about 80%, and its single crystal was obtained with the use of a $CH_2Cl_2$/pentane solvent at −30° C. (1,3-dimethyl-4,5-dimethylimidazole-2-ylidene)(diphenylacetonate) silver was chemically analyzed and the results are as follows:

$^1$H-NMR($CD_2Cl_2$): 3.75 [s, 6H, N(1,3)—$CH_3$], 2.14 [s, 6H, C(4,5)—$CH_3$], 7.89 [m, 4H, Ph], 7.40[m, 6H, Ph], 6.45[s, 1H, C═CH—C]

$^{13}$C-NMR($CD_2Cl_2$): 185.7(s, O—C(Ph)—CH), 179.4(s, $C_{carbene}$), 125.8(s, C═C($CH_3$)—N), 127.4, 128.4, 130.2, 143.8(Ph-group), 93.1(s, C(Ph)═CH═C(Ph)), 36.7(s, C═C($CH_3$)—N), 9.5(s, C═C ($CH_3$))

FT-IR(KBr): 1425, 1466, 1507, 1566, 1605, 1645 cm$^{-1}$
UV/VIS($CH_2Cl_2$): 247, 254 nm

EXAMPLE 1

(1,3-dimethyl-4,5-dimethylimidazol-2-ylidene)(diphenyl acetonate)silver obtained from preparation example 4 was dissolved in methylene chloride to produce a 0.22 M solution, and the solution was coated on a glass substrate under atmospheric air according to a spin coating process at a spin speed varying from 500 rpm/5 sec through 2000 rpm/20 sec to 500 rpm/5 sec. The glass substrate was then exposed to UV light (200 nm to 400 nm) under atmospheric air at a room temperature for 2 hours so as to form a metal pattern. A ligand was separated from a portion exposed to the UV light by the UV light to form a silver metal film on the glass substrate. A portion not exposed to the UV light and photo-decomposed organics remaining on the glass substrate were dissolved with the use of methylene chloride, thus being removed. The resulting glass substrate was put on a hot-plate at about 200° C. and annealed under atmospheric air for about 2 hours to produce a conductive metal pattern. An adhesive force of the metal pattern to the substrate was tested by use of an adhesive tape manufactured by 3M Co., resulting in that the conductive metal pattern was not separated from the substrate. In addition, it was confirmed that an electric current flows through the conductive metal pattern by measuring electric resistance of the conductive metal pattern with the use of a 4-point probe.

TABLE 1

Film thickness and specific resistance varying according to an irradiation time of light

|  | $^2$Thick. (Å) | $^3$Shr. (%) | $^4$Resis. (µΩ) |
|---|---|---|---|
| Before irradiation | 9067 | — | — |
| After 1 hour from irradiation | 5654 | 37.7 | — |
| After 2 hours from irradiation | 4917 | 45.7 | — |
| $^1$Solvent phenomenon | 2655 | 70.7 | 1 × 10$^9$ |
| Heat treatment (200° C., 2 hours) | 1664 | 81.7 | 1.2 × 10$^3$ |

$^1$Solvent phenomenon: Solvent phenomenon (methylene chloride)
$^2$Thick. (Å): Film Thickness (Å)
$^3$Shr. (%): Shrinkage (%)
$^4$Resis. (µΩ): Specific resistance (µΩ)

Preparation Example 5

Synthesis of [(1,3-dimethyl-4,5-dimethylimidazol-2-ylidene) (dimethylacetonate) silver]

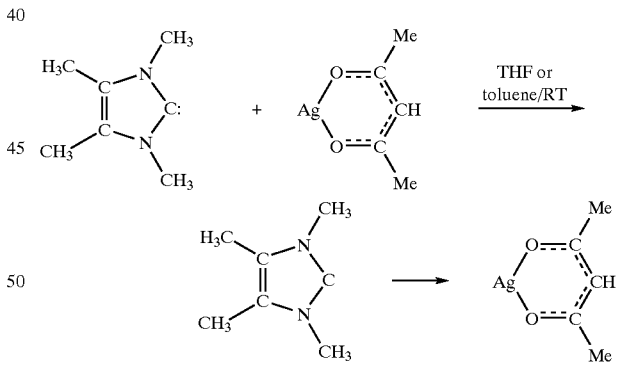

160 mg of 1,3-dimethyl-4,5-dimethylimidazol-2-ylidene (1.29 mmol) obtained from preparation example 2 was added to 30 ml of THF solvent with agitation under a nitrogen atmosphere to be dissolved in the THF solvent. The resulting THF solution of 15 ml was cooled to a low temperature of −78° C., and 242 mg of dimethylacetonate silver slurry obtained from preparation example 3 was slowly added to the cooled THF solution and slowly heated to a room temperature over about 3 hours while agitating the cooled THF solution. After the agitation, fine black precipitates in the solution were then removed by use of a celite, and a solvent was removed under a vacuum to produce a solid. The solid thus produced was dissolved in about 20 ml of methylene chloride and left in a freezer at −30° C. for about one day, and a half of supernatant liquid was slowly added to 100 ml of pentane or hexane solvent by use of a syringe to form a grey solid. After the pentane or hexane solvent containing the grey solid was left for about 1 hour to sufficiently precipitate the grey solid, a light yellow supernatant liquid was removed by use of the syringe. About 50 to 60 ml of hexane and the remaining methylene chloride solution were added to form the grey solid. As described above, after a solution containing the grey solid was left for about 1 hour to sufficiently precipitate the grey solid, a light yellow supernatant liquid was removed by use of the syringe to produce (1,3-dimethyl-4,5-dimethylimidazole-2-ylidene) (dimethylacetonate)silver. (1,3-dimethyl-4,5-dimethylimidazole-2-ylidene) (dimethylacetonate) silver thus produced was chemically analyzed and the results are as follows:

$^1$H-NMR(CD$_2$Cl$_2$): 3.67 [d, 1.2 Hz, 6H, N(1,3)—CH$_3$], 2.12 [d, 0.9 Hz, 6H, C(4,5)—CH$_3$], 1.86[d, 0.9 Hz, 6H, O—C(CH$_3$)—CH], 5.10 [s, 1H, C(CH$_3$)=CH=C(CH$_3$)]

$^{13}$C-NMR(CD$_2$Cl$_2$): 190.8[s, O—C(CH$_3$)—CH], 179.4[s, C$_{carbene}$], 125.8[s, C=C(CH$_3$)—N], 97.4[s, C(CH$_3$)=CH=C(CH$_3$)], 37.0[s, C=C(CH$_3$)—N], 29.3[s, C(CH$_3$)=CH=C(CH$_3$)], 9.5[s, C=C(CH$_3$)]UV/VIS(CH$_2$Cl$_2$): 246, 300 nm

EXAMPLES 2

(1,3-dimethyl-4,5-dimethylimidazol-2-ylidene)(dimethylacetonate)silver obtained from preparation example 5 was dissolved in methylene chloride to produce a 0.2 M solution, and the solution was coated on a glass substrate under atmospheric air according to a spin coating process at a spin speed varying from 500 rpm/5 sec through 2000 rpm/20 sec to 500 rpm/5 sec. The glass substrate was then exposed to UV light (200 nm to 400 nm) under atmospheric air at a room temperature for 2 hours so as to form a metal pattern. A ligand was separated from a portion exposed to the UV light by the UV light to form a silver metal film on the glass substrate. Specific resistance of the silver metal film was measured by use of a 4-point probe, resulting in about 5×10$^9$ μΩ. Meanwhile, the specific resistance of the silver metal film after a solvent phenomenon using methylene chloride was 6×10$^8$ μΩ. After the resulting glass substrate was put on a hot-plate at about 200° C. and annealed under atmosphere for about 2 hours to produce a silver metal film, like in example 1, the specific resistance of the silver metal film was 2.0×10$^2$ μΩ.

As described above, the organometallic precursor of the present invention is advantageous in that a conductive metal pattern can be readily formed through an exposing step without using a separate photo-resist.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. An organometallic precursor for forming a metal pattern, having a structure defined by the following Formula 1:

L'—M—L    Formula 1 wherein, M is a transition metal selected from the group consisting of Ag, Au, Cu, Pd, Ni, and Pt; L is an imidazolylidene compound having a structure defined by the following Formula 2; and L' is an imidazolylidene compound having a structure defined by the following Formula 2 or a β-diketonate compound having a structure defined by the following Formula 3:

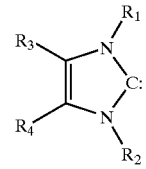

Formula 2 wherein, R$_1$, R$_2$, R$_3$, and R$_4$ are independently a hydrogen atom, or alkyl group, alkenyl group, alkynyl group, carboxyl group, alkoxy group, or ester group with 1 to 20 carbons, or aromatic hydrocarbon group with 6 to 20 carbons; and

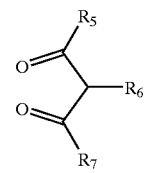

Formula 3 wherein, R$_5$, R$_6$, and R$_7$ are independently a hydrogen atom, or alkyl group, alkenyl group, alkynyl group, carboxyl group, alkoxy group, or ester group with 1 to 20 carbons, or aromatic hydrocarbon group with 6 to 20 carbons.

2. The organometallic precursor according to claim 1, wherein R$_1$, R$_2$, R$_3$, R$_4$, R$_5$, R$_6$, and R$_7$ are independently methyl, ethyl, propyl, isopropyl, isobutyl, or phenyl group.

3. A method of forming a metal pattern, comprising the steps of:

dissolving the organometallic precursor according to claim 1 in a solvent;

coating the resulting solution on a substrate to form a thin film on the substrate;

exposing the thin film through a mask; and developing the thin film to form a metal or a metal oxide pattern on the substrate.

4. The method according to claim 3, wherein the substrate is selected from the group consisting of an inorganic material, an organic material, and a composite thereof.

5. The method according to claim 3, wherein the coating step is conducted according to a spin coating process, a roll coating process, a micro-contact printing process, or a spray coating process.

6. The method according to claim 3, wherein the exposing step is conducted using ultraviolet light as a source of light.

7. The method according to claim 3, further comprising the step of annealing the metal or metal oxide pattern after the developing step.

8. The method according to claim 7, wherein the annealing step is conducted under a mixed gas atmosphere of hydrogen with nitrogen, a pure nitrogen gas atmosphere, or an air atmosphere at 300° C. or lower.

* * * * *